United States Patent
Marks

(10) Patent No.: US 10,426,369 B2
(45) Date of Patent: Oct. 1, 2019

(54) DEVICE AND METHOD FOR LOCALIZATION OF BRAIN FUNCTION RELATED APPLICATIONS

(71) Applicant: Ronald Al Marks, Lancaster, CA (US)

(72) Inventor: Ronald Al Marks, Lancaster, CA (US)

( * ) Notice: Subject to any disclaimer, the term of this patent is extended or adjusted under 35 U.S.C. 154(b) by 0 days.

(21) Appl. No.: 15/962,323

(22) Filed: Apr. 25, 2018

(65) Prior Publication Data

US 2018/0296119 A1 Oct. 18, 2018

Related U.S. Application Data

(62) Division of application No. 13/464,725, filed on May 4, 2012, now Pat. No. 8,898,048.

(Continued)

(51) Int. Cl.
| | | |
|---|---|---|
| A61B 5/0484 | (2006.01) | |
| G16B 5/00 | (2019.01) | |
| G06F 3/01 | (2006.01) | |
| G06T 13/00 | (2011.01) | |
| A61B 5/00 | (2006.01) | |
| G16H 50/50 | (2018.01) | |
| A61B 5/0482 | (2006.01) | |
| A61M 21/00 | (2006.01) | |

(52) U.S. Cl.
CPC ........ *A61B 5/04842* (2013.01); *A61B 5/0482* (2013.01); *A61B 5/04845* (2013.01);
(Continued)

(58) Field of Classification Search
CPC ................................................. A61B 5/04842
(Continued)

(56) References Cited

U.S. PATENT DOCUMENTS 7,510,525 B2 * 3/2009 Kamo ...................... A61B 5/00
600/300

* cited by examiner

*Primary Examiner* — Jerry Lin
(74) *Attorney, Agent, or Firm* — David Kleiman

(57) ABSTRACT

This system is used to rejuvenate youth by targeting the pituitary gland to produce HGH and testosterone. Also, with this system, a personal avatar is created, so that a person with the help of virtual reality, optional, simulate traveling to a specific brain site and giving a stimulation to that site. Also, the personal avatar will travel inside a designated vehicle type for that purpose. Also, The Smart Brain System is a type of a platform that can work with all brain stimulation products. It should become the model that people will use for brain control via the internet. Using this system, the brain is re-wired or re-programmed as to where a stimulation is received within the brain. A person will view a simulation of an electrical stimulation current that transmits to an area of the brain they desire to stimulate. Watching the smart brain simulations enables the mind to have a visual perception of the area of the brain to stimulate. So that by using the mind, vision and sense of hearing and touch, we can show the brain where a stimulation should be received within the brain. Also, using this system will allow the individual to have a more personal role in their brain stimulation therapy. This system can be used in clinical and office settings, although it is primarily for use via the internet. The smart brain system can be produced for use in all languages and marketed to all countries via the internet. The person will log into the smart brain web site. They will be asked to purchase the E-transporter system. It consists of a USB cable that has rectangular panels along its length. These panels are lights, which are programmed to indicate the direction of a current or movement of an object or stimulus within the cable. It will attach at the hand and continue up the arm and onto the back of the neck. Electrode wires with pads branch out at the neck to be placed on the head. This E-transporter and controller have a vibrational capacity, an electrical stimulation capacity, a speech and speech recognition capacity, and a sound effect capacity. It plugs into the computer at the USB port. The user will upload a photo of them self, preferably while wearing the E-transporter, to the web sites database. (This step is optional since a generic photo and E-transporter system can be used). A pre-programmed format will graft a computerized version of the brain into their photo. The therapist or individual will impute the type of brain stimulation they want to generate. When prompted, the program will display a cut-out view of their head displaying the computerized brain inside. When prompted, a pre-programmed video displays a simulated current that transmits to the target region of the brain to be stimulated. When the simulated current enters the target region of the brain, signs and signals will be displayed indicating that the area is being stimulated or that a downloading is in progress. The E-transporter lighting effects, vibrations and tactile properties will work simultaneously with the copy of the E-transporter and simulations that are displayed on the screen. The E-transporter wearable unit and the personal photo enhances the biofeedback that the simulated stimulations are occurring in the individual's own brain. Different concepts of brain design and brain activities can be used. One example would be: simulating the brain as an electronic component and displaying its electronic properties as brain activities. Another example is: simulating the brain as having caves and having a tunnel system that the stimulus travels through etc. The smart brain web site and E-transporter system will be produced by neuroscientists, medical illustrators, computer programmers, video production programmers, graphic designers, business developers, patent attorneys, and many others. Clinical trials are still needed to prove that this type of visual and neuronal feedback is an effective tool for brain stimulation therapy and that it adds a real benefit to brain stimulation therapy that is already being done.

12 Claims, 2 Drawing Sheets

Related U.S. Application Data

(60) Provisional application No. 61/518,454, filed on May 4, 2011.

(52) U.S. Cl.
CPC ........... *A61B 5/4064* (2013.01); *A61M 21/00* (2013.01); *G06F 3/015* (2013.01); *G06T 13/00* (2013.01); *G16B 5/00* (2019.02); *G16H 50/50* (2018.01); *A61M 2021/0072* (2013.01)

(58) Field of Classification Search
USPC .......................................................... 703/11
See application file for complete search history.

DEVICE AND METHOD FOR LOCALIZATION OF BRAIN FUNCTION RELATED APPLICATIONS

BACKGROUND OF THE INVENTION

The present invention relates generally to the art of brain mapping, and more specifically to a device and method for simulating the stimulation of brain areas and neural pathways in a user.

Knowledge of the human brain has increased substantially in recent years. Among the areas of greatest interest to scientists are brain mapping and connectomics. Brain mapping relates the physical structure of the brain to functional properties. This localization of function provides researchers with invaluable information about changes in the brain over time, such as changes due to disease, aging, or physical damage. Brain mapping allows correlation between physical changes and function, opening the door to new possibilities in understanding how disease, aging, injury, and other factors affect the brain physically and, thus, how they impact a person's functional qualities.

Broad functional localizations are well understood by science. For example, it is known that the frontal lobe encompasses thinking, planning, and central executive functions, as well as motor execution. The occipital lobe deals with visual perception and processing, among other things. The temporal lobe handles language functions, auditory perception, emotions, long-term memory, and so on. Although these broad functional categories are of use, scientists are increasingly looking at smaller areas of the brain to determine more specifically the functions that correspond to various physical structures. These endeavors allow scientists to answer increasingly specific questions about how stimuli, physical damage, and the like, to a given area of the brain may impact function.

Connectomics is the study of the specific connections between neurons in an intact brain. The goal is to produce a "wiring diagram" of the brain itself, allowing study of the multitude of individual pathways and connections therein. Complete wiring diagrams have been developed for relatively simple organisms, such as *C. elegans*. Increasingly, scientists are developing wiring diagrams for areas of the human brain.

Brain mapping and the study of the wiring of the brain provide a number of advantages. A more complete picture of the physical structure of the brain allows for greater and more detailed study of the organ. This may allow scientists to understand how humans and other organisms learn and adapt to the environment. Further, greater physical knowledge of the brain can lead to increased safety of neurosurgical procedures, with surgeons having a greater understanding of the effects of the surgery, as well as which portion of tissue to excise and which to leave intact. Further, many disease states have a structural basis in the brain and a greater understanding of brain structure and function can lead to new treatments of these disease states, as well as to methods of observing the efficacy of treatments.

An increased understanding of the structure and function of the brain is also useful to individuals in daily life. For example, the brain undertakes a complex series of behaviors in the formation of habits. First, a trigger event is identified by the brain and interpreted as a signal to enter an "automatic" mode, allowing a specific behavior state to unfold. The brain engages the routine that corresponds to the behavior and, finally, ascertains whether the behavior is rewarded, and therefore whether it is worthwhile as a habit. Habit-forming activities in the brain are based, at least in part, in the basal ganglia, which deal with emotion, memory, and pattern recognition. Decisions that transition from requiring active thought, which takes place in the prefrontal cortex, to habit, in the basal ganglia, free up processing power for other decision-making. The ability to recognize cues and triggers, the corresponding habit behaviors, and the rewards, are of great value in breaking habits. The conscious recognition of what occurs in the brain can lead to increased awareness of a habit, and thereby increase the likelihood that an individual will be able to successfully break the habit.

Brain mapping and awareness of structure and function in the brain may also allow individuals to affect the physical properties of the brain. Neuroscientists have observed, for example, that habitual meditation can strengthen circuits in the brain relating to maintaining concentration or generating empathy. Certain less desirable habits are effectively replaced with new, desirable habits. Awareness of the brain and its functions can provide a benefit to individuals, even if the benefit stems only from the perceived connection to the structure in the brain, and that perception subsequently influences individual behavior.

Finally, brain structure and function is of interest to many in the general public because of a fascination with how the brain works. Such individuals enjoy learning about the various connections and structures in the brain, and how these connections and structures impact their lives.

BRIEF SUMMARY OF THE INVENTION

One aspect of the present invention provides a method of simulating brain activity and neural pathways in a user. The method includes the step of providing a networked server for access by a user of the invention, using a general purpose computer. A database is provided in communication with the networked server. The general purpose computer carries out a step of detecting a movement of the user, the movement then being communicated to the networked server, which associates that movement with a certain set of data in the database relating to predetermined simulated neural activity. The simulated neural activity associated with the user's movement is communicated to the user.

In another aspect of the invention, at least one interface attachment is provided to be worn by the user. The interface attachment is in communication with the general purpose computer, and the simulated neural activity is communicated to the user via the interface attachment.

In another aspect of the invention, the simulated neural activity is communicated to the user by displaying the simulated neural activity on the screen of a general purpose computer. The simulated neural activity is associated with at least a portion of the user's body.

In another aspect of the invention, input is received from the user relating to the simulated neural activity. The user can cause the display of new simulated neural pathways, or the blocking of existing simulated neural pathways, based on the user's input to the system.

In another aspect of the invention, a photograph of the user is received via the general purpose computer and transmitted to the networked server. The simulation of neural activity is displayed to the user as associated with at least a portion of the user's body derived from the photograph.

In another aspect of the invention, the interface attachment is a sleeve, a head piece, or a combination of these.

In another aspect of the invention, a device is provided, the device including an interface attachment sized and shaped to be worn by the user, a stimulator attached to the interface attachment for providing a stimulus to the user, and a data link attached to the interface attachment for transmitting signals to, and receiving signals from, the general purpose computer.

In another aspect of the invention, the stimulator is a light, a speaker, a device for imparting an electric shock to a user, or a combination of these.

In another aspect of the invention, the data link is a USB cable, an Ethernet cable, a wireless communications device, or a combination of these.

In another aspect of the invention, the device includes a plurality of stimulators including a plurality of lights along an exterior surface of the interface attachment. The stimulators are adapted to display patterns of stimulation according to signals receive by the interface attachment via the data link In another aspect of the invention, a method of simulating brain and neurological activity includes providing a networked server for access with a general purpose computer, providing a database in communication with the networked server, accepting a variable from a user, correlating the variable with at least one datum in the database, displaying a simulated image of a portion of the human nervous system on the general purpose computer, determining the portion of the human nervous system impacted by the variable, and animating the portion of the human nervous system determined to be impacted by the variable.

In another aspect of the invention, the variable accepted from the user may be a movement, the name or chemical structure or formula of a drug, or information relating to thoughts, emotions, habits, and the like.

DETAILED DESCRIPTION OF THE INVENTION

Figure 1:
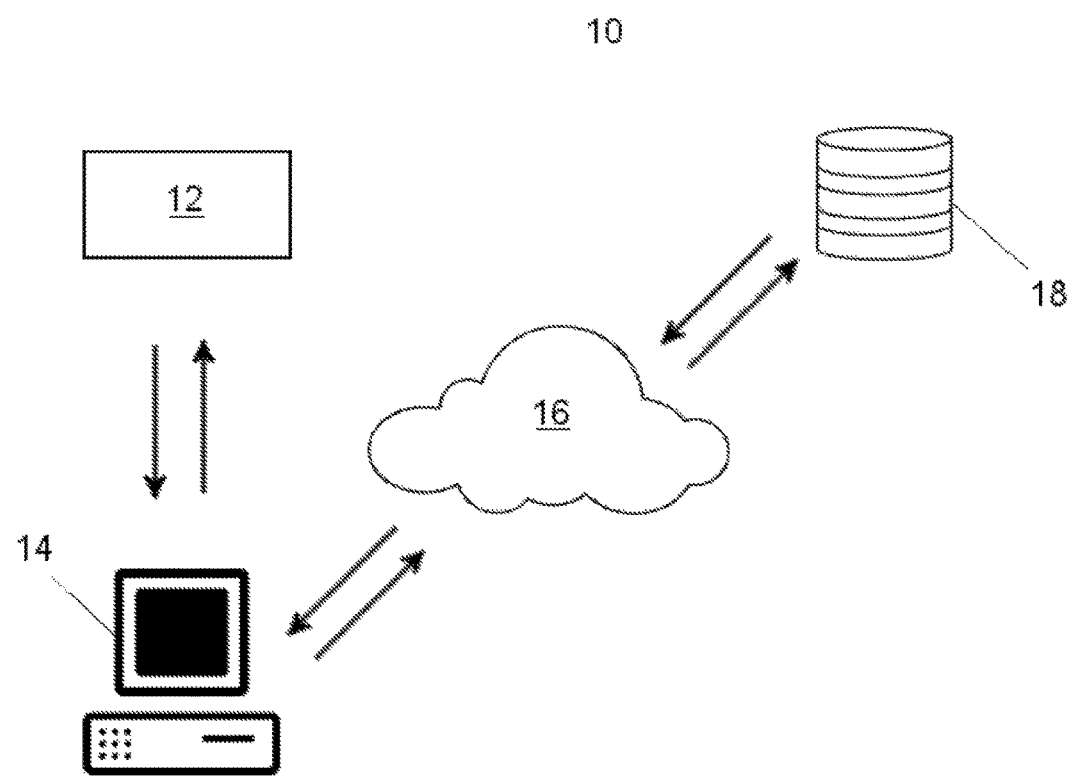
FIG. 1 is a schematic illustration of a system according to the present invention.

It should be noted that some embodiments of the present invention relate to a computing environment, including, but not limited to a web or internet based computing environment. In such embodiments, computing systems for use with the present invention may include any type of computer system, including a general purpose computer, based on a microprocessor, a mainframe computer, a digital signal processor, a portable computing device, a personal organizer, a device controller, or a computational engine within another device. Suitable computer systems include, but are not limited to, personal computers, laptops, tablets, and hand-held phones. For purposes of this writing, the word "general purpose computer" will be used to refer to each of the aforementioned type of device.

As used herein, the word "network" can refer to any type of wired or wireless communication channel capable of coupling two or more computing nodes. Examples include, but are not limited to, local area networks, wide area networks, or a combination of the two. Exemplary networks include the Internet and the Word Wide Web.

In some embodiments of the present invention, a web server may be utilized. Web servers may include any computational node including a mechanism for servicing requests from a client for computational and/or data storage resources. A web server can generally include any system that can host web pages, web sites, web-based applications, or server-side portions of client-server applications.

Embodiments of the present invention may also incorporate a browser. As used herein, the word "browser" includes any application that can display web pages, such as, for example, a web browser. Furthermore, the word "browser" can generally include any system that can interact with web pages be provided using any suitable programming language. Examples of programming languages suitable for use in providing server-side functionality includes, but it not limited to, ASP, Java, Perl, PHP, Python, Ruby, .NET, and combinations of these, web sites, web-based applications, or client-server applications. Embodiments of the present invention wherein aspects of the invention run in a web browser may be developed using any suitable programming language. Examples of such languages include, but are not limited to, Asynchronous JavaScript (Ajax), Flash, JavaScript, Microsoft Silverlight, HTML, HTML5, CSS3, and combinations of these.

Data relating to the present invention may be stored on any non-volatile storage system, including, but not limited to, Magnetic, optical, and magneto-optical storage devices, as well as storage devices based on flash memory and/or battery backed up memory. Data so stored in a database may be distributed across any network used in conjunction with the present invention. Any suitable programming language may be used for managing data in databases associated with the present invention. Examples of such languages include, but are not limited to, Microsoft SQL Server, MySQL, Apache Derby, Oracle, and combinations of these.

Embodiments of the present invention using web-based functionality are preferably secure in order to protect the data of a user of the present system. Security may be provided by, for example, using the Secure Socket Layer (SSL) protocol, which provides for encryption of data transmitted across a network. Web connections for exchange of data preferably employ HTIP Secure (HTIPS), which adds a layer of encryption to communication via the HTIP protocol.

Although as noted above, embodiments of the present invention may be designed to be provided to a user via a web browser, it is contemplated that the functionality of the present invention may be instead provided by a program that is downloaded or otherwise loaded onto a computer system and installed thereon. Such programs may be written in any suitable language, and may be provided for any computer platform, including Windows, Mac OS, iOS, Android, Linux, BSD, Unix, WebOS, and other platforms. Such programs may utilize the internet to communicate with one or more databases used in association with the present invention, or may communicate with databases via a secure link provided solely for that purpose. In addition, it is contemplated that the present invention may be implemented with some combination of web-based service and functionality provided by a computer program installed onto a user's local device.

One aspect of the present invention provides a simulated neural pathway allowing a user to correlate actions and behaviors to the simulated pathway. The simulated neural pathway may be provided via a general purpose computer, being displayed on a screen or monitor associated therewith, and may be provided via a network such as the Internet, or via data contained on a local storage medium. The user of the present invention preferably utilizes an interface device associated with the general purpose computer via any suitable connection, including via a USB connection, Bluetooth, or over a wired or wireless network. Regardless of the type of structure used for communication, this aspect of the present invention may be referred to generally by use of the term "data link." The interface device may indicate activity in a given area of the body, or may provide a stimulus to a given area of the body, or both.

Data for the simulated neural pathway may be stored on any suitable storage medium and is preferably displayed graphically in a manner readily understood by a user of the present device. For example, the computer display utilized may display the image of a human brain, areas of which may be highlighted using color or other suitable indicia to indicate that a given area of the brain is engaged by the user. For example, when a user raises an arm, the portion of the brain that controls the motor function related to raising that arm may be highlighted on the screen. This provides the user with a visual perception of brain function corresponding to the action taken, and allows the brain to make a correlation between the two. The computer display of the brain, with color or other indicia mapped to an area of the brain corresponding to a given action, can assist the user in repeatedly engaging the same part of the brain. It should be understood that this is true even if the area of the brain displayed on the computer display is not the precise portion of the brain actually involved in the action.

Turning to FIG. 1, the interrelations between various components of one embodiment of the present invention is provided. User 12 utilizes a general purpose computer 14 (or, in other embodiments, a mobile device, tablet, or other suitable computing device) programmed to provide the functionality of the present invention, or to access a web server for providing the functionality of the present invention. Information flows both from user 12 to general purpose computer 14, and from general purpose computer 14 to user 12. General purpose computer 14 provides images, text, and other information to user 12 as a result of commands or requests entered by user 12. User 12 may then respond to the information provided by issuing additional commands or requests, initiating new tasks, closing the web browser or other program, or the like. As will be discussed below, in embodiments of the present invention wherein user 12 wears an interface device associated with the present invention, general purpose computer 14 also directs information, such as commands, to the interface device, causing a predetermined response by the interface device.

The interface device of the present invention preferably includes a component worn on a portion of the body of the user of the present invention. This component is able to sense a movement or action on the part of the user and provide a signal to the computer, which in turn provides a corresponding indication on the computer screen to indicate the area of the brain involved in the action. In some embodiments of the invention, the interface device may include a simple sleeve or other structure that slips over a portion of the body, the sleeve or other structure including sensors that are able to register the presence, speed, and directional movement of a user's action. It should be understood, however, that an interface device worn on the body is not required in all embodiments of the present invention. In some embodiments, the interface device may be physically separate from the user, such as when a camera or other device is used. The camera may be used by the present system to identify body movements using technology known in the art, and those body movements may cause a corresponding highlighting of a specific area of the simulated brain shown on the computer monitor.

Figure 2:
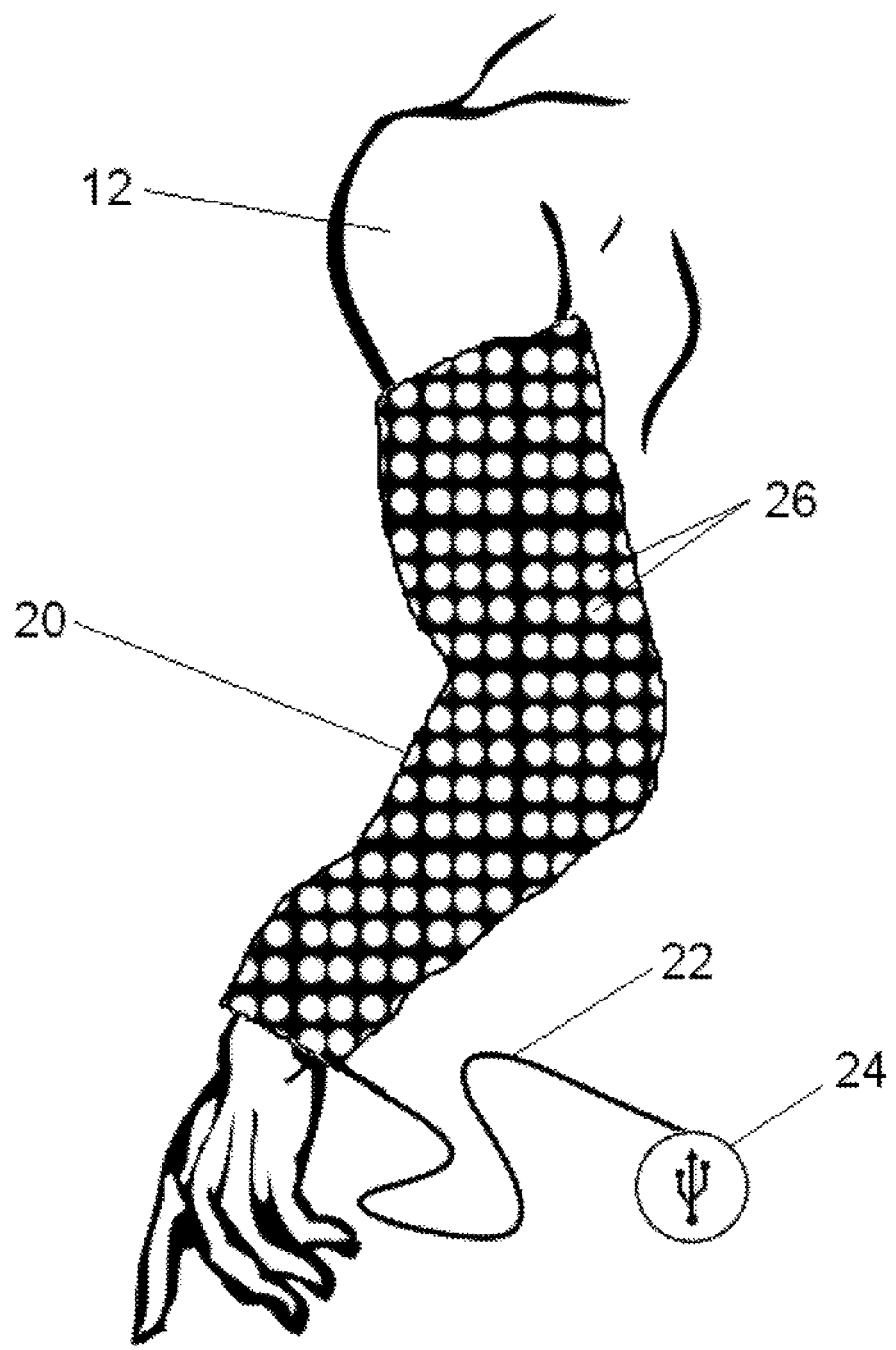
FIG. 2 illustrates one exemplary embodiment of an interface attachment according to the teachings of the present invention.

FIG. 2 provides one embodiment of an interface device of the present invention in the form of sleeve 20. Sleeve 20 slides over an arm of user 12, preferably engaging the arm snugly so that sensors within sleeve 20 can better detect movement of the arm by user 12, as well as to better distinguish various types of movement of the arm by user 12. Sleeve 20 preferably includes a plurality of light-emitting diodes (LEDs) that light up in response to movements by user 12. The LEDs may be arrayed in set paths, such that a single line of LEDs light up in response to a given movement of the arm, thus allowing user 12 to associate in her mind a certain pattern of LEDs with a particular movement. Optionally, the LEDs may also light of flash in various patterns, each pattern corresponding to a given movement of the arm of user 12. These patterns may also be associated in the mind of user 12 with a given arm movement. Further, in some embodiments of the invention, speakers associated with general purpose computer 14 may emit distinctive sounds corresponding to a given movement of the arm of user 12, as well as a pattern of LEDs, thereby engaging additional areas of the brain of user 12 in an attempt to associate the various stimuli with the movement. As also shown in FIG. 2, it is preferred that sleeve 20 include a cord 22 for connecting to a USB port 24 of a computing device. It is contemplated, however, that any suitable method of communication between sleeve 20 and the computing device may be used, including wireless methods of communication.

In addition to the sleeve 20 described above, and other embodiments of an interface attachment described herein, it is contemplated that one embodiment of an interface attachment can extend from a finger of the use to the head of the user, creating an simulated neurological pathways extending over that same area. The interface attachment may include a portion extending over a finger of the user, the portion secured with a Velcro strap or other suitable fastener. Similar straps of fasteners may be used to secure portions of the interface attachment to the forearm and upper arm of the user. The interface attachment may then secure at or near the neck or upper body of the user, and may again extend onto or around the head, where it is also fastened in place. Stimulators may be provided at various points along the length of the interface attachment in order to allow a simulated transmission of stimuli that are meant to simulate a neurological pathway, the path of a drug or medicament, and the like.

As described above, the interface device of the present invention communicates with the computer system in a unidirectional manner. When the interface device senses movement, for example, a signal is sent to the computer implementing the present invention, and the computer system highlights a portion of the simulated brain onscreen corresponding to the signal received from the interface device. It is contemplated, however, that the interface device may work bi-directionally, receiving signals from the computer system as well as transmitting signals to the computer system. When receiving a signal from the computer system, the interface device may respond by performing some function. For example, one embodiment of the interface device may be provided with LEDs or other visual stimuli, as described with respect to sleeve 20, above. Signals received from the computer system of the present invention may direct the interface device to light certain LEDs, such as LEDs 26, or to engage other visual or auditory stimuli. For example, when the user of the present invention lifts an arm, the interface device may send a signal to the computer system indicating that an arm has been lifted. The computer system may then signal the device to light LEDs along the arm of the user. The user now has multiple stimuli to associate with the arm movement, and the brain can correlate those stimuli with that specific movement of the arm. It is contemplated that in some embodiments of the invention, the interface device may produce the visual or other stimuli on its own, without waiting to receive a signal from the computer system. Components of the present invention that provide stimuli to a user, whether visual, auditory, electric, or otherwise, may be referred to generally herein by the term "stimulator."

The interface device may provide other stimuli in addition to, or in place of, visual stimuli. For example, the interface device may provide a vibration at a specific location on the user's body, or may provide a mild electric shock to a specific location on the user's body. In this way, the user involves additional senses in utilizing the present invention to simulate the functional localization of an act to a specific portion of the brain. In addition to visual stimuli from the brain map depicted on the computer display, the user's tactile senses may be engaged by vibration or electric shock to the appropriate area of the body. This use of additional senses can allow the brain to more quickly come to associate a movement or action with a specific region of the simulated brain. It should be noted, of course, that the interface device may employ any combination of visual, auditory, tactile, or other stimuli in order to aid the user in the creation of an association between a single action and engagement of specific loci of the functional brain.

In addition to singular stimuli, or combinations of localized stimuli, the present invention may provide a cycle of stimuli to impact many senses of the user and to create patterns that come to be recognized by the brain. For example, the interface device may include speakers or earphones, either as an integrated part of the interface device or as a separate component of the present invention. When an action is undertaken by a user, the present device may produce a sound played through the speaker or earphone of the device, and may also display a sequence of LEDs and/or produce localized vibrations or vibratory patterns along the body of the user. These patterns of visual, auditory, and tactile sensations may cycle, producing a reoccurrence of the stimuli as often as necessary or desired by the user. The brain of the user can begin to recognize complex patterns of stimuli and associate them with specific actions.

In addition to the interface device described above, the interface device of the present invention may include a series of ribbons or other flexible members extending from a device of the present invention to the body of a user thereof. The flexible members may be attached to the body of the user by use of adhesives or other suitable mechanism. The flexible members may also include a series of lights or other indicia that can be selectively engaged by the computer system of the present invention. The flexible members may be used to simulate a neural pathway, such as by placing the flexible member along an arm or other body part of the user. The flexible member can light up, or engage other selectively engageable indicia, along the body part of the user when that body part is actuated in some manner by the user. The flexible members may also impart vibration or mild electric shock along the path simulated by the flexible member, simulating the transmission of a signal along the simulated neural pathway.

In some embodiments of the present invention, the computer display may also provide an image of the user of the present invention, the image including a mirror image of the flexible members attached to the user's body, the flexible members in the computer-simulated image lighting or engaging other indicia corresponding to the lighting or indicia engaged in the flexible members located on the user's body. Thus, the user is provided with a holistic impression of the various stimuli associated with a given action, experiencing visual, tactile, and/or auditory feedback, or any combination of these, along with the ability to see an overall representation of the visual indicia along the flexible members located on the body. The computer display may also provide a detailed view of the internal neural pathways and wiring of the brain associated with a given action. Again, this imaging on the computer screen is simulated and intended to provide a point of reference to the user. This information may or may not be representative of specific, actual physiological pathways in use, depending on whether the database used in conjunction with the present invention includes such information.

It is contemplated that one embodiment of the present invention is implemented via a web-based service accessible to users via the internet. In such embodiments of the invention a web site is provided where a user can order components of the present invention and/or create an account for use with the present invention. In some embodiments of the invention, the user may create a user account on the web site, creating a password for securely logging into a protected account. The user may select the actions and corresponding areas of the brain desired to be tracked, and may upload to the web serve a photo desired to be used in the display of simulated neural pathways superimposed on the image of the user. In other embodiments of the invention, the web site may simply provide a portal through which a user can order the components of the present invention for use on a local machine. A photograph or other representation of the user can be transmitted via mail, such as on a CD or other storage medium, and the resulting image with superimposed neural pathways can be provided to the user in the same manner, or can be made available via the web site. In other embodiments of the present invention, a web cam may be used to take a photograph of the user while using the present invention, the photograph then being uploaded directly to a web server utilized by a provider of the present invention.

The user, via the interface device and the computer display having the image of the user thereon, along with a simulated brain and/or neural pathways, can now suspend disbelief and allow himself to accept that he is connected to various areas of his own brain as simulated by the interface device and the onscreen image. The user can then undertake actions, such as movement, and allow his brain to absorb the pattern of interactions created and correlate the patterns with the action taken.

In addition to actions such as movement of a body part, a user of the present invention may associate certain thoughts, moods, and emotions with simulated neural pathways and with certain areas of the brain. For example, the user may choose to bind certain keys or key combinations to specific simulated pathways and structural areas of the simulated brain. These keys or key combinations may also be associated with given thoughts, moods, emotions, and the like. When the user experiences the thoughts, moods, or emotions desired to be tracked, the user can use the key or key combination to engage a series of auditory, visual, tactile, or other stimuli. The brain can then begin to associate the pattern of stimuli with the mood, thought, or emotion. A user can then reinforce positive mental images, feelings, and the like, particularly through the use of pleasant stimuli. In the same manner, negative thoughts, feelings, images, and the like can be disfavored, particularly through the use of negative stimuli. Even where the stimuli themselves are not positive or negative, the awareness created by the brain's association of the thoughts, moods, or emotions with certain simulated neural pathways or portions of the brain may be of value to the user.

In still other embodiments of the present invention, the invention is used to create a game for a user. In some of these embodiments of the invention, the computer display may provide an extremely close view of the simulated neural pathway at issue, allowing the user a visual representation as though the user is actually traveling along those pathways. The user may be given the option to create new pathways that were not previously in existence or to travel to areas of the brain locked by the initial programming of the system, representing areas of the brain previously inaccessible to the user. Thus, the user is able to symbolically forge new pathways in the brain, or to access those areas of the brain that were previously inaccessible. This symbolic achievement may aid the user in achieving certain goals with respect to the mind, such as enhanced awareness, or fighting undesirable habits or unwanted thoughts in the mind. The game provided by the present invention has no direct affect on the brain of the user, but can instead provide psychological motivation and positive reinforcement to the user. These can be useful in altering existing thought patterns, moods, emotions, and the like. Further, the present invention may allow the user to achieve a feeling or impression of external control of the brain, despite being aware of the simulated nature of the invention. This feeling of control can be empowering and can aid the user in addressing the unwanted actions, thoughts, moods, emotions, and the like being addressed with the present invention.

In some embodiments of the invention, it is contemplated that a web site provided by a provider of the present invention includes information relating to the functioning of the brain, brain activity, the effects of drugs and other medicaments on the brain and central nervous system, and the like. The information can be displayed to the user to provide education about various aspects of brain structure and function, as well as about neurological function in general. In embodiments of the present invention, an image of a brain may be superimposed over the image of the user, and as the user accesses information regarding the structure and function of the brain, locations on the superimposed image of the brain may be highlighted to indicate structural and functional aspects and relationships of the brain that correlate with the information the user is accessing.

The database associated with the web site of a provider of the present invention may also include detailed information on various psychoactive drugs and other medicaments. This information may also be utilized to provide textual and graphical information to a user of the present invention. When a given drug is selected by the user, the image of the superimposed, simulated brain may be highlighted to show the area of the brain impacted by use of the chosen drug. If more than one drug is chosen, different colored highlights may be used to distinguish the pathways and areas of activity of each drug. These pathways may be animated as well, showing a simulated depiction of the action of the drug in the body and it travels through areas of the brain, or as it leaves the brain and moves into other areas of the body. In embodiments of the invention wherein a picture of the user's body is also represented in the image provided onscreen, areas of the user's body may also be highlighted to show the simulated travel of a drug through the body, or the action of a drug at a particular region of the body.

In other embodiments of the invention, the user can, in a simulated fashion, trace the flow of neurological activity, or the activity of a drug, along the user's own body. The image onscreen may illustrate this through animation and highlighting, and the interface attachment worn by the user may engage a stimulator (as described above; for example, an LED, a device to generate a mild electric shock, and the like). The movement of the stimulus along the interface device can coincide with the animation of the path of a drug or neurological activity shown on the computer screen. The user can associate this simulated path of activity with a given thought or action which the user wishes to identify with a given pathway.

EXAMPLE

The following is an example of one game embodiment of the present invention. It should be noted that the following example is intended to be illustrative of the present invention and is not intended to be limiting.

In this game embodiment of the invention, the user wears an arm piece that is, in essence, a tubular sleeve that extends from the user's fingers to the base of the neck. The sleeve may also be attached to a ring, collar, or other structure that extends around a user's head. The sleeve and the structure extending around the user's head have electrical conductive properties, allowing varying levels of electrical stimulation to be imparted to the skin of the user. The sleeve and apparatus extending around the head may also include a vibration effect, allowing the user to experience localized vibrations from the device. A lighting system on the components of the invention correlates with the electrical shock and/or vibrational pathways of the device, allowing the user to visualize as well as feel stimuli from the components.

The user provides a photo of himself, either by upload via the internet or by sending an image, digital or otherwise, to a provider of the present system. The photo is used to produce a silhouette or largely transparent image of the user, onto which an image of the human brain and/or neural pathways is superimposed. The image so provided can be enlarged or animated to show all of the features selected by the user utilizing the present invention, and also to indicate the various neural pathways and regions of the brain, as well as the underlying functions of each.

Using the game aspect of the present invention, the user simulates a stimulus to an area of the brain, thereby creating an impression of use or engagement of that area of the brain. A mild electrical shock is provided along the sleeve and the structure extending around the head, creating a simulated nerve transmission that the user can feel. According to the visualization on the computer screen, the user can see the impulse traveling to the same area of the brain desired to be engaged. This can be seen on the computer screen as well as on the other components of the device actually worn by the user. Animations may be used to show stimulation to the area at issue, and to see the stimulation of positive responses in the brain.

The game aspect of the present invention may be incorporated into any game on the market in order to show positive responses to the brain when desired effects are achieved within the context of the game.

Another aspect of the invention makes available an external interactive brain system. In this embodiment of the invention, a robot or automaton is provided wearing an interface device on its body corresponding to an interface device worn by the user of the present invention. The interface device provided on the automaton can reproduce all of the properties seen by the user when using the present invention, as well as those images seen by the user when watching the computer screen. The robotic implementation of the present invention can be used to further enhance the perception that a certain region of the brain is being stimulated.

While particular embodiments of the present invention have been shown and described, it will be obvious to those skilled in the art that based upon the teachings herein, that changes and modifications may be made without departing from this invention and its broader aspects. Therefore, the appended claims are to encompass within their scope all such changes and modifications as are within the true spirit and scope of the invention.

The invention claimed is:

1. A system for displaying an animated simulation of neurological activity of a system user comprising:
   a) a user-computer having an input device and display;
   b) a system server having a system processor and system storage memory;
   c) a network connection between the user computer and the system server;
   d) a neurological database in the system storage memory;
   e) said neurological database containing at least one user-condition datum stored in a relation to at least one affected nervous system portion datum;
   f) at least one operating instruction in said system storage memory for the system server to receive from said user-computer over said network connection a user-condition input;
   g) at least one operating instruction in said system storage memory for the system server to receive from said user-computer over said network connection a user-photograph;
   h) at least one operating instruction in said system storage memory for determining from a correlation of said user-condition input and said at least one user-condition datum in said neurological database a related user-affected nervous system portion; and
   i) at least one operating instruction in said system storage memory for the system server to transmit to said user-computer display over said network connection an animated image that comprises a combination of said related user-affected nervous system portion and at least a portion of said user-photograph.

2. The system for displaying a simulation of neurological activity of a system user of claim 1 where said at least one user-condition datum represents a user physical movement.

3. The system for displaying a simulation of neurological activity of a system user of claim 1 where said at least one user-condition datum represents a user drug.

4. The system for displaying a simulation of neurological activity of a system user of claim 1 where said at least one user-condition datum represents a user emotion.

5. The system for displaying a simulation of neurological activity of a system user of claim 1 where said at least one user-condition datum represents a user thought.

6. The system for displaying a simulation of neurological activity of a system user of claim 1 where said at least one user-condition datum represents a user habit.

7. A system for displaying an animated simulation of neurological activity of a system user comprising:
   a) a user-computer having an input device and a display;
   b) said user-computer having a system processor and system storage memory;
   c) a neurological database in the system storage memory;
   d) said neurological database containing at least one user-condition datum stored in a relation to at least one affected nervous system portion datum;
   e) at least one operating instruction in said system storage memory for receiving a user-condition input;
   f) at least one operating instruction in said system storage memory for receiving a user-photograph;
   g) at least one operating instruction in said system storage memory for determining from a correlation of said user-condition input and said at least one user-condition datum in said neurological database a related user-affected nervous system portion; and
   h) at least one operating instruction in said system storage memory to display on said display device an animated image that comprises a combination of said related user-affected nervous system portion and at least a portion of said user-photograph.

8. The system for displaying an animated simulation of neurological activity of a system user of claim 7 where said at least one user-condition datum represents a user physical movement.

9. The system for displaying an animated simulation of neurological activity of a system user of claim 7 where said at least one user-condition datum represents a user drug.

10. The system for displaying an animated simulation of neurological activity of a system user of claim 7 where said at least one user-condition datum represents a user emotion.

11. The system for displaying an animated simulation of neurological activity of a system user of claim 7 where said at least one user-condition datum represents a user thought.

12. The system for displaying an animated simulation of neurological activity of a system user of claim 7 where said at least one user-condition datum represents a user habit.

* * * * *